(12) United States Patent
Parent et al.

(10) Patent No.: US 11,957,801 B2
(45) Date of Patent: Apr. 16, 2024

(54) METHOD AND DEVICE FOR A POLYESTER STERILIZATION PROCESS

(71) Applicant: EVONIK CORPORATION, Parsippany, NJ (US)

(72) Inventors: Edward Parent, Dallas, TX (US); Boris Obermeier, Hattersheim (DE); Jie Lu, Norwalk, CT (US)

(73) Assignee: Evonik Corporation, Piscataway, NJ (US)

( * ) Notice: Subject to any disclaimer, the term of this patent is extended or adjusted under 35 U.S.C. 154(b) by 166 days.

(21) Appl. No.: 16/758,819

(22) PCT Filed: Oct. 23, 2018

(86) PCT No.: PCT/US2018/057080
§ 371 (c)(1),
(2) Date: Apr. 23, 2020

(87) PCT Pub. No.: WO2019/083985
PCT Pub. Date: May 2, 2019

(65) Prior Publication Data
US 2020/0316236 A1 Oct. 8, 2020

Related U.S. Application Data

(60) Provisional application No. 62/575,846, filed on Oct. 23, 2017.

(51) Int. Cl.
A61L 2/26 (2006.01)
A61L 2/08 (2006.01)
B65D 81/18 (2006.01)

(52) U.S. Cl.
CPC ............. *A61L 2/087* (2013.01); *A61L 2/26* (2013.01); *B65D 81/18* (2013.01); *A61L 2202/182* (2013.01); *A61L 2202/21* (2013.01)

(58) Field of Classification Search
CPC ...... A61L 2/087; A61L 2/26; A61L 2202/181; A61L 2202/182; A61L 2202/21;
(Continued)

(56) References Cited

U.S. PATENT DOCUMENTS 4,986,414 A 1/1991 Ashley et al.
8,252,228 B1 8/2012 Freeman et al.
(Continued)

FOREIGN PATENT DOCUMENTS

CN 1600382 A 3/2005
CN 105923213 A 9/2016
(Continued)

OTHER PUBLICATIONS

PCT International Search Report and The Written Opinion of the International Searching Authority dated Feb. 19, 2019 corresponding to PCT Application No. PCT/US2018/057080 filed Oct. 23, 2018 (11 pages).
(Continued)

Primary Examiner — Timothy C Cleveland
(74) Attorney, Agent, or Firm — Linda S. Li; Jason S. Ngui; Andrew H. Chung

(57) ABSTRACT

Described herein are packages for orienting and cooling polyesters during a sterilization process, and containers for storing, transporting, and cooling the package. Also described herein are methods of sterilizing polyesters.

5 Claims, 7 Drawing Sheets

(58) Field of Classification Search
CPC .... B65D 81/18; B65D 81/20; B65D 81/2007; B65D 81/2023; B65D 81/2069; B65D 81/2084
See application file for complete search history.

(56) References Cited

U.S. PATENT DOCUMENTS

| | | | |
|---|---|---|---|
| 8,887,477 | B2 | 11/2014 | Falotico et al. |
| 2005/0003007 | A1 | 1/2005 | Boix et al. |
| 2011/0031657 | A1 | 2/2011 | Minbiole et al. |
| 2012/0045362 | A1 | 2/2012 | Kleiner et al. |

FOREIGN PATENT DOCUMENTS

| | | |
|---|---|---|
| JP | 2009543596 A | 12/2009 |
| JP | 2013540462 A | 11/2013 |
| NL | 7511590 A | 4/1977 |
| NO | 174994 B | 5/1994 |
| RU | 2017500 C1 | 8/1994 |
| RU | 2012104884 A | 8/2013 |
| WO | 2005077360 A2 | 8/2005 |
| WO | 2008008436 A1 | 1/2008 |
| WO | 2011006877 A1 | 1/2011 |
| WO | 2016071919 A1 | 5/2016 |
| WO | WO-2016166323 A1 * 10/2016 ............. B62D 33/02 |  |

OTHER PUBLICATIONS

Loo, J.S.C. et al., "Degradation of poly(lactide-co-glycolide) (PLGA) and poly(I-lactide) (PLLA) by electron beam radiation," Biomaterials, vol. 26, Jun. 24, 2004, pp. 1359-1367.

* cited by examiner

METHOD AND DEVICE FOR A POLYESTER STERILIZATION PROCESS

This Application is a 35 U.S.C. § 371 U.S. national stage of PCT International Application No. PCT/US18/057080, filed Oct. 23, 2018, which claims the benefit of U.S. Provisional Patent Application No. 62/575,846, filed Oct. 23, 2017, the contents of each of which are hereby incorporated by reference in their entirety into this application.

BACKGROUND

Biomaterials that are intended for medical applications are in need of sterilization prior to use. One sterilization technique is through the use of electron beam (E-beam) radiation. However, E-beam sterilization of biomaterials, such as biodegradable polyesters, may cause deleterious side-effects that can hinder their use.

SUMMARY

In one aspect, the invention provides a package for orienting and cooling a polyester during a polyester sterilization process. The package includes a plurality of packets each containing polyester granules, and a housing defining a receptacle for receiving the plurality of packets. The housing defines a top region disposed above the receptacle, a bottom region disposed below the receptacle generally opposite the top region, and a plurality of sides disposed around the receptacle between the top region and the bottom region. The housing includes at least one divider disposed between adjacent packets for separating the packets, and a compartment disposed in at least one of the plurality of sides. The compartment receives a coolant. The coolant is not disposed directly above the receptacle and is not disposed directly below the receptacle such that the receptacle can be irradiated from top to bottom or bottom to top without radiation passing through the coolant.

In another aspect, the invention provides methods of sterilizing a polyester, the method comprising irradiating a polyester having a glass transition temperature ($T_g$) with an electron beam, wherein the polyester is maintained at a temperature below its $T_g$ by a coolant, and wherein the electron beam does not pass though the coolant.

In another aspect, the invention provides methods of sterilizing a polyester, the method comprising irradiating a polyester with an electron beam, wherein the polyester is packaged in a packet substantially free of oxygen.

DETAILED DESCRIPTION

Figure 1:
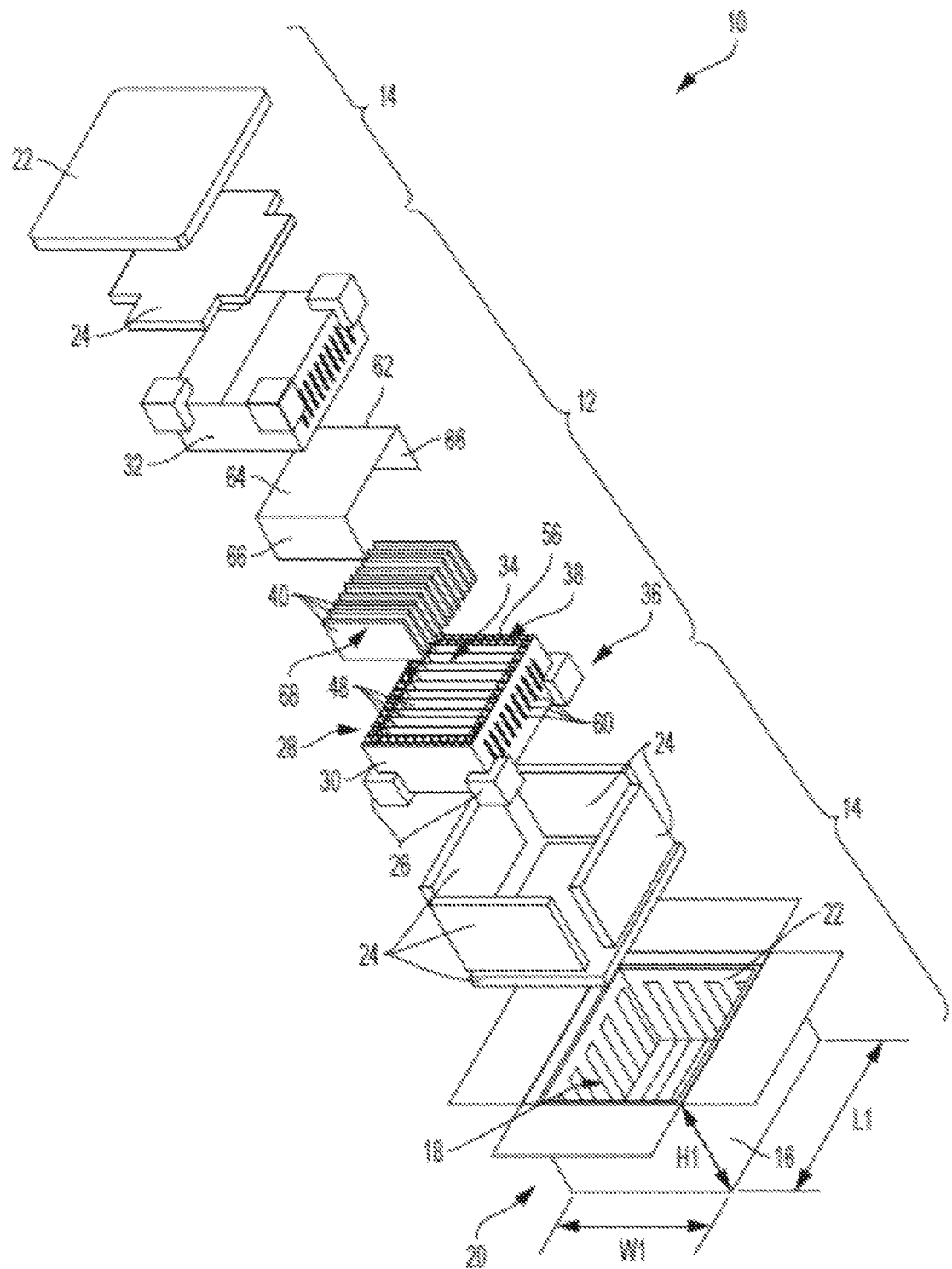
FIG. 1 is an exploded view of a packaging system having a package for orienting and cooling a polyester during a sterilization process and a container for storing and transporting the package.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term substantially oxygen-free, or substantially free of oxygen, is defined herein as mostly oxygen free, or close to oxygen free in view of the inherent limitations of vacuum packing processes in their ability to remove oxygen from a space. Substantially oxygen-free may refer to oxygen being present at less than 5 ppm, less than 4 ppm, less than 3 ppm, less than 2 ppm, less than 1 ppm, less than 0.9 ppm, less than 0.8 ppm, less than 0.7 ppm, less than 0.6 ppm, less than 0.5 ppm, less than 0.4 ppm, less than 0.3 ppm, less than 0.2 ppm, less than 0.1 ppm, less than 0.05 ppm, less than 0.01 ppm, or 0 ppm.

2. PACKAGING SYSTEMS

FIG. 1 illustrates a packaging system 10 having a package 12 for orienting and cooling a polyester during a sterilization process and a container 14 for storing, transporting, and cooling the package 12.

The container 14 includes a frame 16, such as a cardboard box or other structure or material defining an interior 18 and an exterior 20. The frame 16 may be formed from other paper products or from other materials, such as a polymer, in other constructions. The frame 16 generally defines an enclosure for the package 12 on the interior 18 of the frame 16. In the illustrated construction the frame 16 is a six-sided parallelepiped, such as a rectangular cuboid. In other constructions, the frame 16 may have other shapes. In the illustrated construction, the container 14 has overall dimensions of about 26 inches (length L1) by about 15 inches (height H1) by about 24 inches (width W1). The term "about" should be understood to mean plus or minus 2 inches when referring to dimensions of the packaging system, package, container, etc. In other constructions, the length L1 is 22 to 30 inches, the height H1 is 11 to 19 inches, and the width W1 is 20 to 28 inches. In yet other constructions, any suitable dimensions are possible, such as no more than 60 inches in any direction.

The frame 16 may include an insulating liner 22, such as a STYROFOAM® (e.g., closed-cell extruded polystyrene foam) liner or other suitable insulation material that is less heat conductive than the frame material. The insulating liner 22 may be disposed adjacent one or more of the six sides of the frame 16, interiorly of the frame 16. In the illustrated construction, the insulating liner 22 is disposed inside all six sides of the frame 16. In other constructions, the insulating liner 22 may be disposed exteriorly of the frame 16. The container 14 also includes a container coolant 24, such as dry ice (carbon dioxide), disposed adjacent the liner 22, interiorly of the frame 16. The container coolant 24 may include any suitable form of dry ice, such as pellets, slabs, etc. In other constructions, the container coolant 24 may include other substances, such as ice blankets, gel ice packs, etc. The container coolant 24 may be disposed adjacent one or more of the six sides of the insulating liner 22. In the illustrated construction, the container coolant 24 is disposed inside all six sides of the insulating liner 22.

Corner blocks 26 provide a gap between the package 12 and the container 14 when the package 12 is received in the container 14. The corner blocks 26 also secure the package 12, as will be described in greater detail below. The corner blocks 26 may be formed from a foam material, or any other suitable material. In the illustrated construction, eight corner blocks 26 are employed. However, in other constructions, the number of corner blocks 26 may vary as is best suited for varied geometries of the container 14 and the package 12.

The package 12 includes a housing 28 (FIGS. 1-4), which may include a base 30 and/or a lid 32 defining an interior 34 and an exterior 36. In the illustrated construction the housing 28 is a six-sided parallelepiped, such as a rectangular cuboid, but may have other geometries and other numbers of sides in other constructions. In the illustrated construction, the package 12 has overall dimensions of about 20 inches (length L2) by about 8 inches (height H2) by about 17 inches (width W2). In other constructions, the length L2 is 16 to 24 inches, the height H2 is 4 to 12 inches, and the width W2 is 13 to 21 inches. In yet other constructions, any suitable dimensions are possible, such as no more than 48 inches in any direction.

Figure 2:
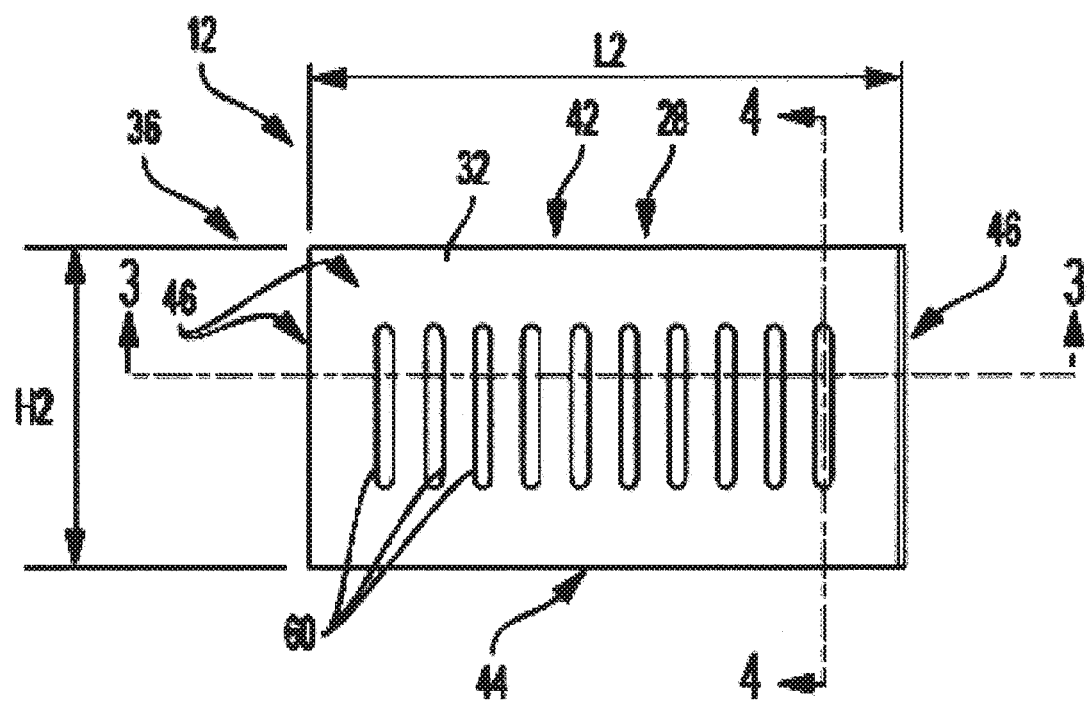
FIG. 2 is a side view of the package of FIG. 1.
Figure 3:
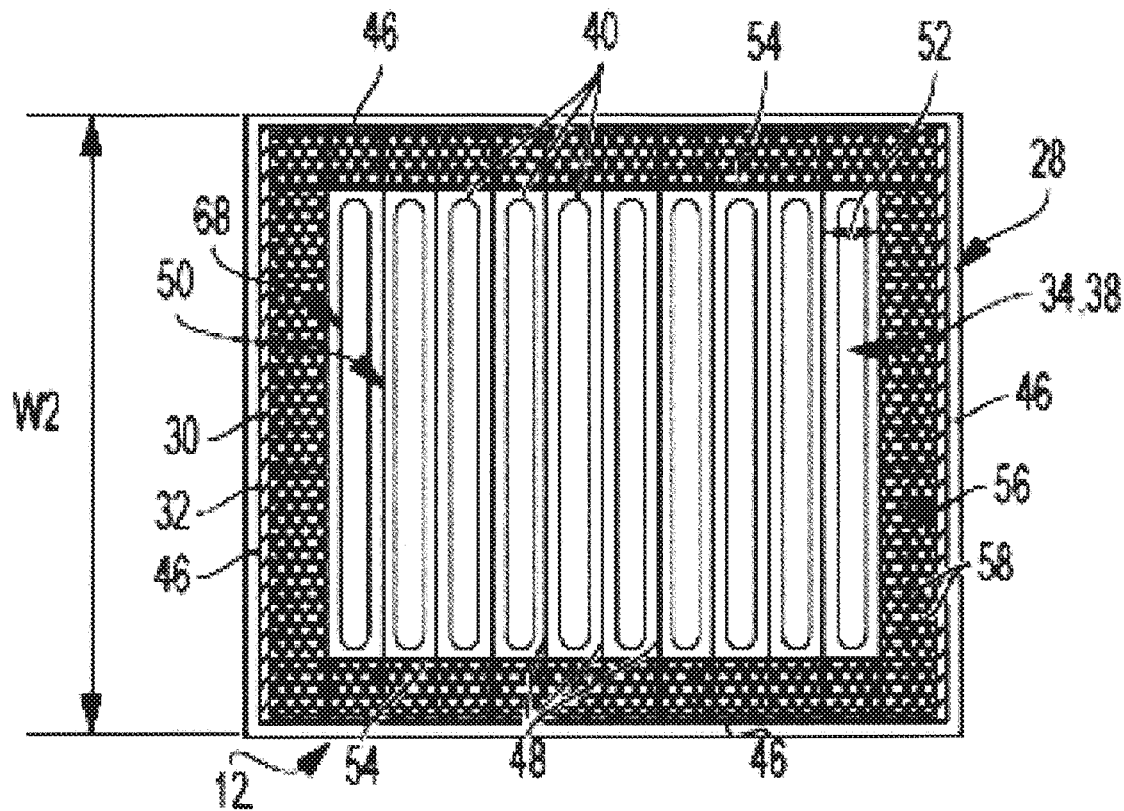
FIG. 3 is a cross-section view of the package taken along line 3-3 in FIG. 2.
Figure 4:
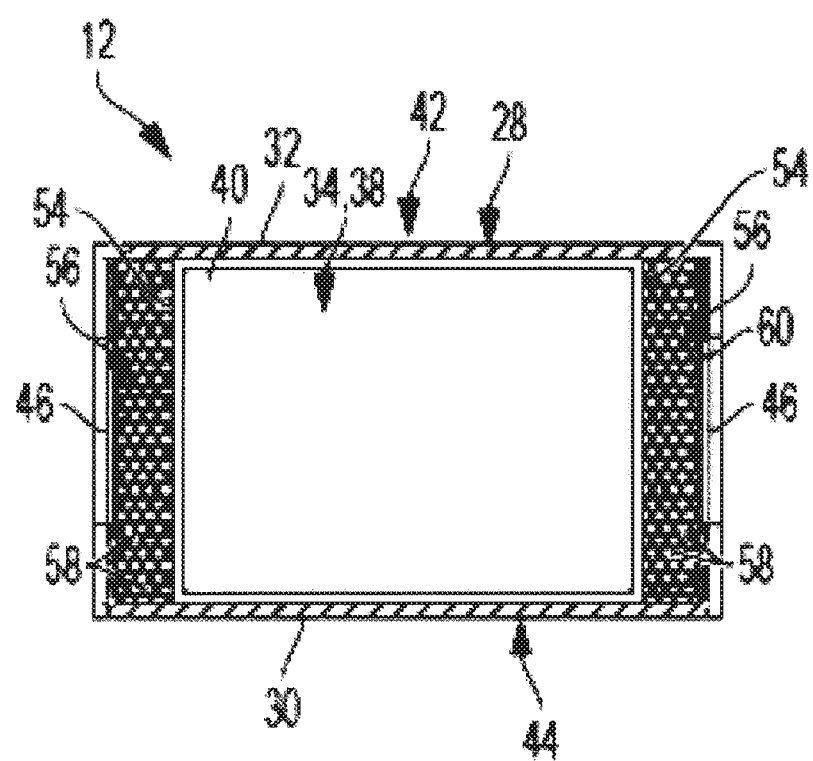
FIG. 4 is a cross-section view of the package taken along line 4-4 in FIG. 2.

The housing 28 defines a receptacle 38 for receiving a plurality of packets 40 (which will be described in greater detail below) on the interior 34. With reference to FIG. 2, the housing 28 generally defines a top region 42 (e.g., a first of the six sides) disposed above the receptacle 38, a bottom region 44 (e.g., another of the six sides opposite the first side) disposed below the receptacle 38 generally opposite the top region 42, and a plurality of sides 46 (e.g., the remaining of the six sides) disposed around the receptacle 38 between the top region 42 and the bottom region 44. The plurality of sides 46 generally form an annulus around the receptacle 38 between the top region 42 and the bottom region 44. It should be understood that the terms "top", "bottom", "above", and "below", as may be used herein, are relative terms based on any fixed reference point and do not require an orientation with respect to gravity. Rather, these terms generally define the regions and directions relative to each other.

Figure 5:
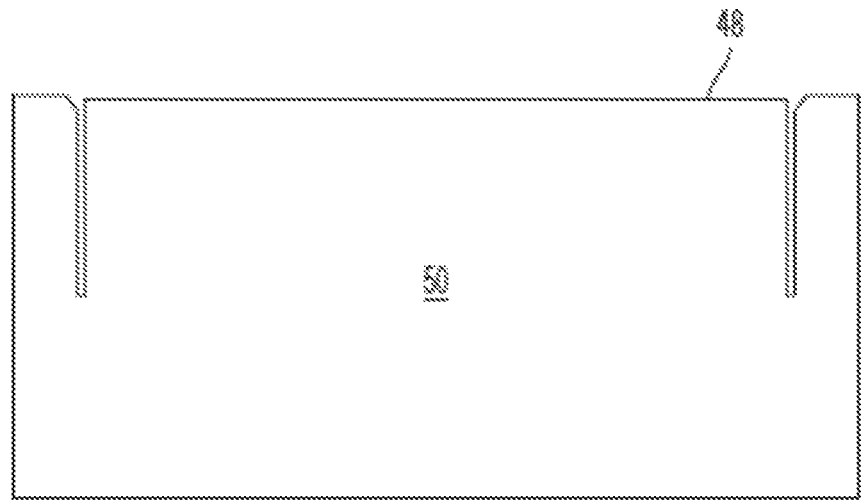
FIG. 5 is a plan view of a first divider for the package of FIG. 2.
Figure 6:
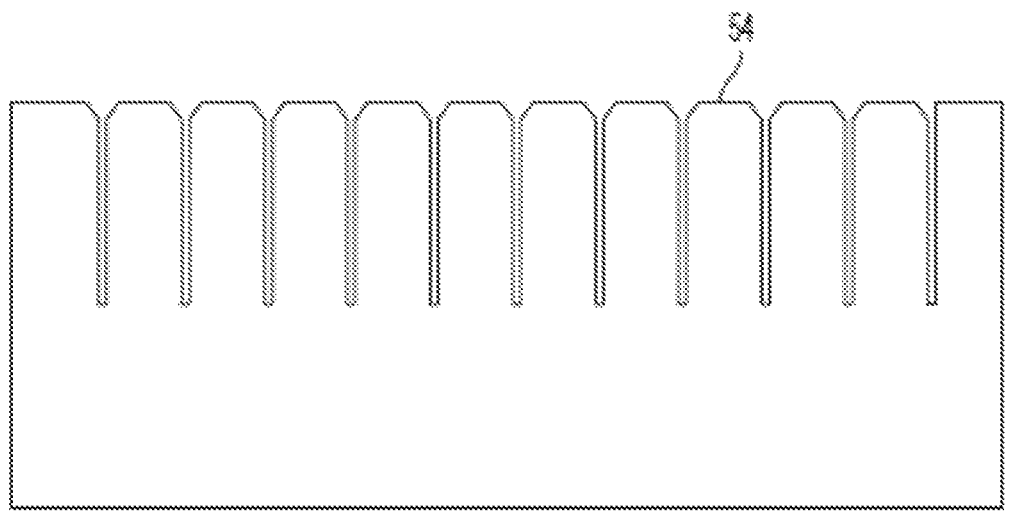
FIG. 6 is a plan view of a second divider for the package of FIG. 2.

The package 12 includes at least one divider 48 (or insert) disposed between adjacent packets 40 for separating the packets 40. In the illustrated construction, the at least one divider 48 includes a plurality of dividers 48 having substantially planar faces 50 (FIG. 5). The dividers 48 are arranged face-to-face and parallel to each other in a row within the receptacle 38, defining a gap 52 between each pair of adjacent dividers 48 in which one of the packets 40 is disposed. In the illustrated construction, each gap 52 is 1 to 2 inches (e.g., about 1.5 inches), but may be larger or smaller in other constructions. The row of dividers 48 extends in a direction from one of the plurality of sides 46 to another of the plurality of sides 46, which may be opposite sides. In the illustrated construction, 10 packets are disposed between 11 dividers. However, in other constructions, any suitable number of packets 40 may be employed. For example, between 8 and 12 packets, between 6 and 14 packets, etc., may be employed in other constructions. The package 12 also includes a pair of inserts 54 (FIG. 3 and one shown in FIG. 6) disposed transverse to the plurality of dividers 48 (e.g., perpendicularly to the plurality of dividers 48).

The package 12 also includes a compartment 56 (FIGS. 1, 3 and 4) disposed in at least one of the plurality of sides 46. The compartment 56 may extend along a portion of one of the plurality of sides 46, along one of the plurality of sides 46, along two of the plurality of sides 46, along three of the plurality of sides 46, or along all of the plurality of sides 46. For example, the compartment 56 is disposed in all four of the plurality of sides 46 of the housing 28, forming an annulus surrounding the receptacle 38 on the sides 46 but not the top 42 or bottom 44, as illustrated in FIG. 1. The compartment 56 may be defined between the dividers 48 disposed at the ends of the receptacle 38 and the housing 28, and further between the inserts 54 and the housing 28. In other constructions, other inserts, dividers, walls, or structures may be employed to separate the compartment 56 from the receptacle 38.

The compartment 56 receives a coolant 58, such as dry ice (carbon dioxide), disposed interiorly of the housing 28 and exteriorly of the receptacle 38. The coolant 58 may include any suitable form of dry ice, such as pellets, slabs, etc. In other constructions, the coolant 58 may include other substances. The coolant 58 is not disposed directly above the receptacle 38 and is not disposed directly below the receptacle 38 such that the receptacle 38 can be irradiated from top to bottom or bottom to top without radiation passing through the coolant 58, as will be described in greater detail below.

The housing 28 includes a plurality of vents 60 in fluid communication with the compartment 56 for venting the coolant 58. In the illustrated construction, the vents 60 are formed as apertures in the base 30 and the lid 32, each vent 60 having the form of a generally elongated slot extending in a direction from top to bottom. Ten vents 60 are employed in the illustrated construction, such that one vent 60 is provided for each packet 40. However, in other constructions, the number, size, and shape of the vents 60 may vary and need not correspond with the packets 40.

The package 12 also includes a tray 62 (FIG. 1) that covers the receptacle 38 (and therefore covers the packets 40) and inhibits the inundation of coolant 58 from the compartment 56 into the receptacle 38. The tray 62 includes a cover portion 64, which may be substantially planar, disposed above the receptacle 38 for covering the receptacle 38. The dimensions of the cover portion 64 generally match the corresponding dimensions of an upper boundary of the receptacle 38. The tray 62 also includes flaps 66 depending from the cover portion 64, which may be transverse to the cover portion 64. The flaps 66 extend into the receptacle 38 directly adjacent the dividers 48 at the ends of the receptacle 38. Thus, the tray 62 secures the packets 40 in the receptacle 38 and provides a barrier inhibiting the coolant 58 from entering the receptacle 38. The tray 62 may be formed from a paper product, such as cardboard, card stock, etc., or from other suitable materials in other constructions, such as a polymer, fibers, etc. When the package 12 is disposed within the container 14, the corner blocks 26 secure the package 12 in the container 14 to inhibit the coolant 58 from moving to the receptacle 38 holding packets 40.

Each packet 40 defines first and second packet faces 68, the packets 40 being arranged face-to-face with respect to each other and with respect to the adjacent dividers 48. The packets 40 may be formed from a foil, a polymer, or other suitable material, and each contains polyester granules (which will be defined in greater detail below) to be sterilized in a process that will be described in greater detail below. Each packet 40 is vacuum packed and sealed such that the polyester granules are in a substantially oxygen-free environment inside the packet 40.

3. METHODS OF STERILIZING A POLYESTER

Disclosed herein are methods of sterilizing polymers and in particular polyesters through the use of electron beam radiation. In one aspect, disclosed are methods of sterilizing a polyester, the method comprising irradiating a polyester having a glass transition temperature ($T_g$) with an electron beam, wherein the polyester is maintained at a temperature below its $T_g$ by a coolant, and wherein the electron beam does not pass though the coolant.

During electron beam sterilization large amounts of energy can be introduced to the polymer to be sterilized. This energy can have the effect of generating heat which can raise the polymer's temperature and cause fusion of the polymer. Cooling the polymer (e.g., below its $T_g$) during sterilization may minimize fusion in the samples. However, the polymer cannot be packed directly in the coolant because this can cause electron absorption and scatter, which can cause irregularities in the dose applied to the polymer being sterilized. The disclosed methods by keeping the polyester below its $T_g$ and not having the electron beam pass through the coolant can alleviate the issues of polymer fusion during sterilization. Accordingly, in the disclosed methods the polyester (e.g., in granule form) may not fuse together during irradiation.

The methods may use varying dosages of electron beam irradiation. For example, the polyester may be irradiated at about 10 kGy to about 300 kGy, such as about 15 kGy to about 250 kGy, about 10 kGy to about 200 kGy, or about 15 kGy to about 50 kGy. In some embodiments, the polyester may be irradiated at greater than 10 kGy, greater than 12 kGy, greater than 15 kGy, or greater than 17 kGy. In some embodiments, the polyester may be irradiated at less than 300 kGy, less than 250 kGy, less than 200 kGy, or less than 150 kGy.

The polyester may be any polyester that is susceptible to agglomerating under increased temperatures, as well as any polyester that is susceptible to oxygen mediated polymer chain scission and/or cross-linking of polymer chains. Examples of polyesters include, but are not limited to, polylactic acid, polyglycolic acid, polycaprolactone, poly(dioxanone), poly(trimethylene carbonate), copolymers of polylactic acid, polyglycolic acid and/or polycaprolactone (e.g., poly(lactic-co-glycolic acid)—PLGA), copolymers of PLGA and polyethylene glycol (PEG), copolymers of PLGA and poly(dioxanone), copolymers of PLGA and poly(trimethylene carbonate), and combinations thereof. In some embodiments, the polyester may be polylactic acid, PLGA or combinations thereof. The polyester may have a $M_w$ of about 1 kDa to about 500 kDa, such as about 2 kDa to about 400 kDa or about 3 kDa to about 300 kDa. In addition, in embodiments including a copolymer, the copolymer may have varying feed ratios of different monomers depending on the intended goal of the final product.

In addition, the polyester may be present in a variety of different forms. For example, the polyester may be present in the form of granules, powder, pellets, bulk or combinations thereof. The polyester may also be packaged in a packet as described above, and the packet may be substantially free of oxygen. In some embodiments, the polyester may be in the form of granules, the granules being packaged in a packet substantially free of oxygen. The packet may be substantially free of oxygen due to it being vacuum sealed. In some embodiments, the packet may be vacuum sealed and then purged with an inert gas, such as nitrogen and/or argon. In other embodiments, the packet may be purged with an inert gas and then vacuum sealed. The packet may comprise an inner pouch and an outer pouch. The inner pouch may comprise polyethylene, nylon or a combination thereof. The outer pouch may comprise foil.

The packet may have advantageous properties that allow it to be useful for the irradiation of polyesters. For example, the inner pouch may have a seal strength of about 10 lbf/in to about 15 lbf/in before, during and/or after electron beam irradiation. In addition, the outer pouch may have a seal strength of about 13 lbf/in to about 20 lbf/in before, during and/or after electron beam irradiation. The seal strength value of the inner pouch and outer pouch may be measured via any side of the pouch (e.g., top, bottom, etc.).

The disclosed methods may allow the polyester to avoid oxygen-mediated side-effects induced by electron beam radiation, such as chain scission and/or cross-linking of polymer chains. Accordingly, the disclosed methods may allow the polyester to maintain certain physical properties during the irradiation process, such as inherent viscosity, molecular weight, and/or polydispersity. For example, the polyester following irradiation may have a change in inherent viscosity of about 0% to about 15% relative to the polyester's inherent viscosity prior to irradiation, such as a change of about 0.1% to about 13% or a change of about 0% to about 12% relative to the polyester's inherent viscosity prior to irradiation. In addition, the polyester following irradiation may have a change in $M_w$ of about 0% to about 20% relative to the polyester's $M_w$ prior to irradiation, such as a change of about 0.1% to about 17% or a change of about 0% to about 16% relative to the polyester's $M_w$ prior to irradiation.

The methods may use a number of different coolants (as described above) to maintain the temperature of the polyester below its $T_g$. For example, suitable coolants include, but are not limited to, dry ice, ice blankets, gel ice packs, or combinations thereof. In some embodiments, the coolant may be dry ice.

The method may further include adding the polyester to a package as described above prior to irradiating. For example, the method may further include adding the polyester to a package prior to irradiating wherein the package comprises a housing defining a receptacle for receiving a plurality of packets and further defining a top region disposed above the receptacle, a bottom region disposed below the receptacle generally opposite the top region, and a plurality of sides disposed around the receptacle between the top region and the bottom region, the housing including at least one divider disposed between adjacent packets for separating the packets, and a compartment disposed in at least one of the plurality of sides, the compartment receiving the coolant, wherein the coolant is not disposed directly above the receptacle and is not disposed directly below the receptacle such that the receptacle can be irradiated from top to bottom or bottom to top without radiation passing through the coolant.

In another aspect, disclosed herein are methods of sterilizing a polyester, the method comprising irradiating a polyester with an electron beam, wherein the polyester is packaged in a packet substantially free of oxygen.

Generally, the above-description regarding the polyester, the packet, the dosages of electron beam irradiation, and polyester properties following irradiation are applicable to the methods comprising irradiating a polyester with an electron beam, wherein the polyester is packaged in a packet substantially free of oxygen. For the purposes of brevity, this description will not be repeated here.

4. EXAMPLES

Nomenclature for Polymers Used in Examples 1 & 2

Polymer 1: Poly(D,L-lactide)—IV of 0.22 dL/g—$M_w$ of 19 kDa;
Polymer 2: Poly(D,L-lactide)—IV of 0.33 dL/g—$M_w$ of 32 kDa;
Polymer 3: Poly(D,L-lactide-co-glycolide)—IV of 0.20 dL/g—$M_w$ of 18 kDa—feed ratio of lactide:glycolide 50:50;
Polymer 4: Poly(D,L-lactide-co-glycolide)—IV of 0.37 dL/g—$M_w$ of 41 kDa—feed ratio of lactide:glycolide 50:50;
Polymer 5: Same as Polymer 3 and also being densified;
Polymer 6: Same as Polymer 4 and also being densified;
Polymer 7: Poly(D,L-lactide-co-glycolide)—IV of 0.20 dL/g—$M_w$ of 14 kDa—feed ratio of lactide:glycolide 75:25;
Polymer 8: Poly(D,L-lactide-co-glycolide)—IV of 0.38 dL/g—$M_w$ of 38 kDa—feed ratio of lactide:glycolide 75:25;
Polymer 9: Branched Poly(D,L-lactide-co-glycolide) with a glucose initiator—IV of 0.50 dL/g $M_w$ of 66 kDa—feed ratio of lactide:glycolide 55:45.

Example 1—Electron Beam Sterilization Experiment I

The most direct effect of degradation of polymers is loss of molecular weight and reduced inherent viscosity. Unexposed and exposed samples were tested using the harmonized inherent viscosity (IV) method that samples were dissolved in chloroform (0.1% w/v) at 25° C. and measured in an Ubbelhode capillary. Specifically, three different packing methods were performed: 1) vacuum packing, 2) vacuum packing with $N_2$ purge and 3) air packing. Samples from different packing methods were sterilized via E-beam irradiation at two different dosages, 40 kGy and 200 kGy. IV data of the exposed materials is listed in Table 1. As shown in entries 1-3, after E-beam exposure, the air packing sample has a lower IV compared to vacuum packing and vacuum packing with $N_2$ purge samples. When increasing the dosage from 40 kGy to 200 kGy, the IV of the vacuum packing sample stays at 0.29 dL/g (entry 4). However, the IV of the air packing sample decreased further to 0.25 dL/g (entry 5). This indicates that oxygen removal can be responsible for reducing polymer degradation. A similar trend was observed on the sterilization of Polymer 10. It is further observed that the IV drop in the vacuum packing sample (entry 6) is less than the one in the air packing sample (entry 7).

Due to chain scission and degradation caused by the electron beam treatment, the IV was expected to significantly decrease with increasing dose, however the reduction in IV was minimal. It is hypothesized that the vacuum packing of the samples reduced the amount of oxygen free radicals thereby reducing the amount of free radical damage.

TABLE 1

Packing impact on E-beam sterilization of Polyesters

| Product description | Entry | Packing | IV (dL/g) |
|---|---|---|---|
| Polymer 4 at 40 kGy dosage | 1 | Vacuum | 0.29 |
|  | 2 | Vacuum + $N_2$ | 0.29 |
|  | 3 | Air | 0.28 |
| Polymer 4 at 200 kGy dosage | 4 | Vacuum | 0.29 |
|  | 5 | Air | 0.25 |
| Polymer 10 at 200 kGy dosage | 6 | Vacuum | 0.37 |
|  | 7 | Air | 0.32 |

Example 2—Electron Beam Sterilization Experiment II

This example further evaluates the impact of electron beam sterilization on multiple polymers. Specifically, this experiment evaluated several control release polymers, and examined their changes in appearance, molecular weight, and inherent viscosity of the polymer. Seal strength of the package was also tested.

Methods

Receipt of Materials: Polymer samples were received from the sterilization facility and stored at refrigerated conditions. Table 2 below lists the polymers received.

TABLE 2

Polymers received for Example 2

| Product | Quantity |
|---|---|
| Polymer 1 | 100 gram |
| Polymer 2 | 100 gram |
| Polymer 3 | 2 × 100 gram |
| Polymer 4 | 2 × 100 gram |
| Polymer 7 | 100 gram |
| Polymer 8 | 100 gram |
| Polymer 9 | 200 gram |

Samples were received intact with no visible defects. Samples were cold to the touch and were placed in storage at 4° C.

Packaging:

Twenty grams of sample as listed in Table 3 were packaged in polyethylene/nylon pouches as the inner packing and foil lined pouches. Both inner and outer pouches were vacuum-sealed

TABLE 3

Packaged samples with labeling

| Product Name | Quantity |
|---|---|
| Polymer 1 | 4 × 20 gram + Retain |
| Polymer 2 | 4 × 20 gram + Retain |
| Polymer 3 | 4 × 20 gram + Retain |
| Polymer 4 | 4 × 20 gram + Retain |
| Polymer 5 | 4 × 20 gram + Retain |
| Polymer 6 | 4 × 20 gram + Retain |
| Polymer 7 | 4 × 20 gram + Retain |
| Polymer 8 | 4 × 20 gram + Retain |
| Polymer 9 | 4 × 20 gram + Retain |

Shipping:

Three of each sample listed in Table 3 were collected and one set of each sample was grouped and placed in a bag with a specific exposure dose labeled for that bag. The label on each sample was marked with the exposure dose so as not to mix them up after exposure. The exposure doses were 17.5 kGy, 25 kGy, and 35 kGy. The packages were stored in the refrigerator at 4° C. before placing them in a qualified shipper with 8 frozen cold packs. The samples were stored at 4° C. until dosing.

Dosing:

The samples were stored at 4° C., sorted and dosed with electron beam irradiation at 17.5 kGy, 25 kGy, and 35 kGy. The samples were then returned to the cold room and were shipped in the same qualified shippers with 8 frozen ice packs.

Receipt of Materials Post-Electron Beam Treatment:

The samples were received cold and removed from the foil pouch. It was noticed (in some samples) that there was an agglomeration of the materials that occurred. The agglomeration appeared to increase with increasing dose. The samples were opened and approximately 2-3 grams of each sample were placed into labeled glass vials with plastic screwcaps to send for analysis.

Results

The exposed samples along with one set of retained un-exposed samples were sent to analytical for testing of IV and gel permeation chromatography (GPC) (chloroform as the solvent and calibrated against polystyrene standards). The results are listed in Table 4 below.

TABLE 4

Analytical results from the impact studies

| Product/Exposure | IV (dL/g) | | | | Mw (kDa) | | | | Mn (kDa) | | | | PDI | | | |
|---|---|---|---|---|---|---|---|---|---|---|---|---|---|---|---|---|
| kGy | 0 | 17.5 | 25 | 35 | 0 | 17.5 | 25 | 35 | 0 | 17.5 | 25 | 35 | 0 | 17.5 | 25 | 35 |
| Polymer 1 | 0.22 | 0.22 | 0.22 | 0.21 | 19 | 18 | 18 | 16 | 12 | 11 | 10 | 6.2 | 1.6 | 1.7 | 1.8 | 2.6 |
| Polymer 2 | 0.33 | 0.31 | 0.30 | 0.30 | 32 | 29 | 29 | 29 | 20 | 18 | 17 | 16 | 1.6 | 1.7 | 1.7 | 1.8 |
| Polymer 3 | 0.20 | 0.20 | 0.20 | 0.20 | 18 | 15 | 15 | 15 | 10 | 4.8 | 4.6 | 4.7 | 3.4 | 3 | 3.3 | 3.2 |
| Polymer 4 | 0.37 | 0.34 | 0.34 | 0.33 | 41 | 36 | 36 | 36 | 24 | 21 | 20 | 20 | 1.7 | 1.7 | 1.8 | 1.8 |
| Polymer 5 | 0.20 | 0.20 | 0.20 | 0.20 | 16 | 15 | 15 | 15 | 5 | 5.3 | 4.8 | 4.7 | 3.1 | 2.9 | 3.2 | 3.2 |
| Polymer 6 | 0.37 | 0.35 | 0.35 | 0.35 | 41 | 38 | 38 | 38 | 24 | 22 | 22 | 22 | 1.7 | 1.7 | 1.8 | 1.8 |
| Polymer 7 | 0.20 | 0.19 | 0.20 | 0.19 | 14 | 14 | 13 | 13 | 5.1 | 5.3 | 4.7 | 4.7 | 2.7 | 2.6 | 2.9 | 2.8 |
| Polymer 8 | 0.38 | 0.35 | 0.34 | 0.34 | 38 | 34 | 34 | 34 | 21 | 19 | 19 | 19 | 1.8 | 1.8 | 1.8 | 1.8 |
| Polymer 9 | 0.50 | 0.46 | 0.46 | 0.46 | 66 | 66 | 57 | 58 | 36 | 36 | 30 | 30 | 1.8 | 1.8 | 1.9 | 2.0 |

All analytical data was reviewed, and the integration of some of the original GPC data was re-evaluated in order to normalize the baselines in which discrepancies can result in erroneous results.

It was noticed that there were some skewed results due to the analytics of the $M_n$ and polydispersity caused by "tailing" on the GPC for low molecular weight acid polymers. This is a known issue of GPC for these polymers. This is pronounced in the data for Polymer 3, Polymer 5 and Polymer 7 that gave high PDI. These data can be used as relative data to show trends.

Inherent Viscosity:

The most direct effect of degradation of polymers is loss of molecular weight and reduced inherent viscosity. Due to chain scission and degradation caused by the electron beam treatment, the IV was expected to significantly decrease with increasing dose, however the reduction in IV was minimal. Similar to Example 1, it is hypothesized that the vacuum packing of the samples reduced the amount of oxygen free radicals thereby reducing the amount of free radical damage. The data in Table 5 lists the IV of the pre-exposed and exposed materials along with the specification for that product. There was minimal effect on the IV and all of the product IV's remained within the range of the specification.

TABLE 5

Product specification and the product IV at various E-beam doses

| Product/kGy | Specification | IV (dL/g) | | | |
|---|---|---|---|---|---|
| | | 0 | 17.5 | 25 | 35 |
| Polymer 1 | 0.16-0.24 | 0.22 | 0.22 | 0.22 | 0.21 |
| Polymer 2 | 0.25-0.35 | 0.33 | 0.31 | 0.30 | 0.30 |
| Polymer 3 | 0.16-0.24 | 0.20 | 0.20 | 0.20 | 0.20 |
| Polymer 4 | 0.32-0.44 | 0.37 | 0.34 | 0.34 | 0.33 |
| Polymer 5 | 0.16-0.24 | 0.20 | 0.20 | 0.20 | 0.20 |
| Polymer 6 | 0.32-0.44 | 0.37 | 0.35 | 0.35 | 0.35 |
| Polymer 7 | 0.14-0.22 | 0.20 | 0.19 | 0.20 | 0.19 |
| Polymer 8 | 0.30-0.44 | 0.38 | 0.35 | 0.34 | 0.34 |
| Polymer 9 | 0.45-0.60 | 0.50 | 0.46 | 0.46 | 0.46 |

Figure 7:
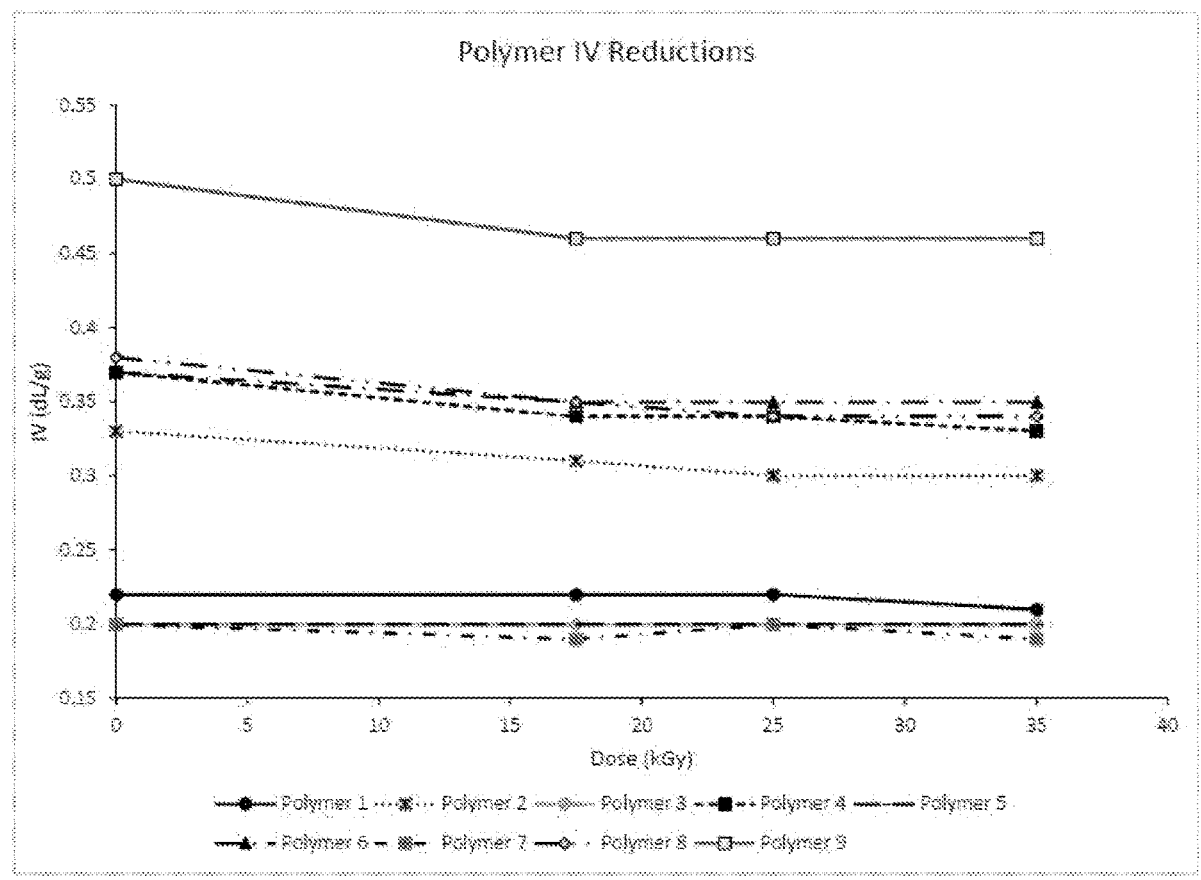
FIG. 7 is a plot showing the effect of E-beam dose on inherent viscosity (IV) of different polyesters.

The effects can also be seen graphically in FIG. 7. It is noted that larger changes in IV are realized by polymers with higher starting IV.

Particle Fusion:

Electron beam sterilization is a preferred method of sterilizing polymeric materials because of the low amount of heat generated. Some heat generated can be calculated from the specific heat for the polymer. Using the equation $\Delta^\circ$ C.=0.239*kGy/h, and h=0.27964 cal/g ° C. and 0.5497 cal/g ° C. (as disclosed by Thomas S, Yang W, Advances in Polymer Processing: From Macro—To Nano—Scales. Cambridge UK: Woodhead Publishing: 2009: p. 414—which is incorporated by reference herein in its entirety) the maximum increase in polymer temperature at 35 kGy was expected to be between about 15.2° C. to about 29.9° C.

Figure 8:
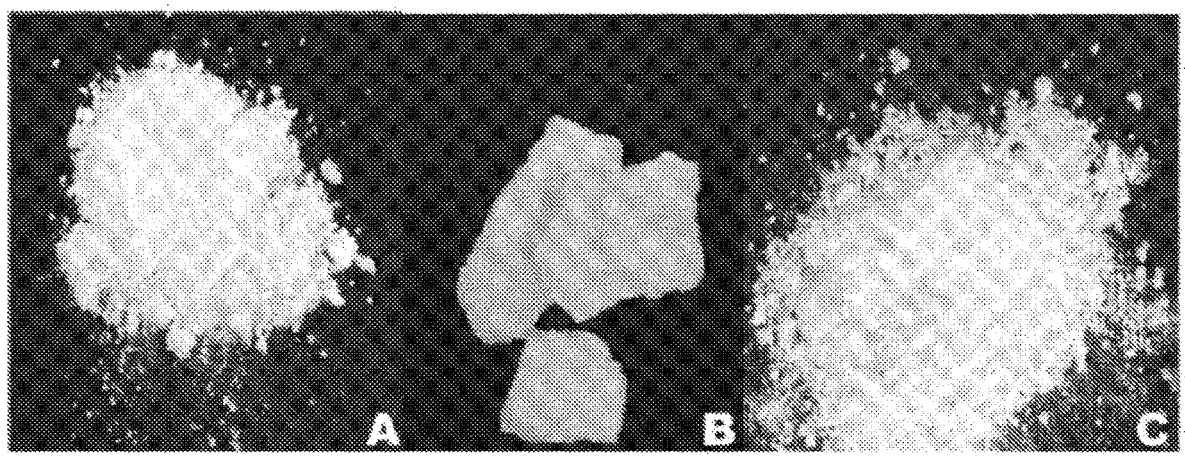
FIG. 8 is a series of images showing A: untreated polyester; B: 25 kGy treated polyester; and C: 25 kGy treated polyester with dry ice as a coolant.

The polymer was placed in the sterilizer at 4° C., however, fusion occurred even at lower doses. It was assumed that the fusion occurred because the temperature increased above the glass transition temperature. The higher than expected temperature change may be caused by the structure of the system, such as the packing and foil lined coating. To avoid this fusion a second set of materials were sent with the instruction to pack in dry ice. The samples exposed in dry ice showed no fusion, even at 35 kGy. (See FIG. 8).

Closure System:

20 gram samples of Polymer 9 were packaged in packets as described above. Exposed and un-exposed samples were analyzed via ASTM F88/F88M—15 Standard Test Method for Seal Strength of Flexible Barrier Materials. The results indicated that there were small variations in seal strength from pouch to pouch on the outer closure with no dose dependence on the electron beam sterilization (see Table 6). The inner pouches showed no significant variability. This data is supported by manufacturer's data on the closure system. Accordingly, the closure system should be suitable for sterilization of polyesters.

TABLE 6

Seal strength of tested pouches

| | Peak value (lbf/in) | | | | | | | |
|---|---|---|---|---|---|---|---|---|
| | INNER POUCH | | | | OUTER POUCH | | | |
| Dose (kGy) | Bottom | Left | Top | Right | Bottom | Left | Top | Right |
| 0 | 12.56 | 12.81 | 13.59 | 12.82 | 16.97 | 17.26 | 17.42 | 18.88 |
| 17.5 | 12.81 | 12.73 | 13.17 | 13.07 | 15.15 | 17.93 | 16.68 | 19.23 |
| 25 | 12.85 | 12.44 | 13.67 | 13.08 | 15.59 | 17.62 | 15.16 | 17.96 |
| 35 | 12.82 | 12.91 | 13.72 | 13.24 | 15.76 | 19.38 | 17.96 | 18.04 |

This example studied the effect of electron beam sterilization at the dose of 17.5, 25, and 35 kGy on polymers. The doses of 17.5 or 25 kGy are expected to be suitable for sterilization based on estimated bioburden, and 35 kGy would represent an excess exposure. Ionization sterilization can produce free radicals that can cause chain scissions, cross-linking, or a combination of both, which can be reflected in an increase or decrease in the polymer molecular weight. Since the IV is proportional to the molecular weight, similar changes should be visible for IV.

At all doses, the IV values either remained unchanged or demonstrated a slight decrease. All of the polymer IVs remained within the original specification as seen in Table 5. There is a similar decrease in the molecular weight that was noticed, as can be seen table 7. The polymers with the higher molecular weight saw the highest percentage reduction in molecular weight.

Packing shows to be suitable at the doses tested. The samples were vacuum sealed to reduce the oxygen content and thereby reducing the effects of oxygen free radicals, which is hypothesized to be a protective factor during E-beam sterilization.

In addition, while all of the product IVs remained in specification, it was seen that products sterilized at ambient temperature showed physical fusion due to heat generated by the process. This problem was mitigated by the inclusion of dry ice in the system and process.

TABLE 7

Percent Change in Molecular Weight

| | Percent change in Mw | | | |
|---|---|---|---|---|
| Product/kGy | 0 | 17.5 | 25 | 35 |
| Polymer 1 | 0.0% | −5.3% | −5.3% | −15.8% |
| Polymer 2 | 0.0% | −9.4% | −9.4% | −9.4% |
| Polymer 3 | 0.0% | 0.0% | 6.3% | −6.3% |
| Polymer 4 | 0.0% | −12.2% | −12.2% | −12.2% |
| Polymer 5 | 0.0% | −6.3% | −6.3% | −6.3% |
| Polymer 6 | 0.0% | −7.3% | −7.3% | −7.3% |
| Polymer 7 | 0.0% | 0.0% | −7.1% | −7.1% |
| Polymer 8 | 0.0% | 0.0% | −10.5% | −10.5% |
| Polymer 9 | 0.0% | 0.0% | −13.6% | −12.1% |

Example 3—Electron Beam Sterilization Experiment III

An in-process cooling carrier was developed for polymers exposed to electron beam irradiation. The carrier holds the samples in a specific orientation relative to the electron beam. The carrier also holds the coolant in a specific orientation such that the coolant is isolated from the electron beam that will pass through the samples. The samples are therefore cooled such that the heat generated from the electron beam does not cause agglomeration, aggregation or fusion of the sample. In this case, the samples sterilized are usable as a pourable powder or granular substance.

Samples of polylactic acid polymer and polylactide-co-glycolide acid polymer were packaged as powder or granular form. The samples were packaged in a cardboard box. The box was placed in another box with a physical barrier to prevent mixing with the coolant. Materials were sent for exposure to electron beam sterilization at 17.6, 25, 35, 50, 100, or 200 kGy. The results of electron beam sterilization can be seen in in Table 8.

TABLE 8

Fusion Analysis Following Electron Beam Irradiation

| Polymer | Lactide Molar % | Glycolide Molar % | Inherent Viscosity (dL/g) | Dose (kGy) | Cooling | Fusion (yes/no) |
| --- | --- | --- | --- | --- | --- | --- |
| polylactic acid | 100 | 0 | 0.22 | 17.5 | no | yes |
| polylactic acid | 100 | 0 | 0.22 | 17.5 | dry ice | no |
| polylactic acid | 100 | 0 | 0.22 | 25 | no | yes |
| polylactic acid | 100 | 0 | 0.22 | 25 | dry ice | no |
| polylactic acid | 100 | 0 | 0.22 | 35 | no | yes |
| polylactic acid | 100 | 0 | 0.22 | 35 | dry ice | no |
| polylactic acid | 100 | 0 | 0.33 | 17.5 | no | yes |
| polylactic acid | 100 | 0 | 0.33 | 17.5 | dry ice | no |
| polylactic acid | 100 | 0 | 0.33 | 25 | no | yes |
| polylactic acid | 100 | 0 | 0.33 | 25 | dry ice | no |
| polylactic acid | 100 | 0 | 0.33 | 35 | no | yes |
| polylactic acid | 100 | 0 | 0.33 | 35 | dry ice | no |
| polylactide-co-glycolide | 50 | 50 | 0.20 | 17.5 | no | yes |
| polylactide-co-glycolide | 50 | 50 | 0.20 | 17.5 | dry ice | no |
| polylactide-co-glycolide | 50 | 50 | 0.20 | 25 | no | yes |
| polylactide-co-glycolide | 50 | 50 | 0.20 | 25 | dry ice | no |
| polylactide-co-glycolide | 50 | 50 | 0.20 | 35 | no | yes |
| polylactide-co-glycolide | 50 | 50 | 0.20 | 35 | dry ice | no |
| polylactide-co-glycolide | 50 | 50 | 0.37 | 17.5 | no | yes |
| polylactide-co-glycolide | 50 | 50 | 0.37 | 17.5 | dry ice | no |
| polylactide-co-glycolide | 50 | 50 | 0.37 | 25 | no | yes |
| polylactide-co-glycolide | 50 | 50 | 0.37 | 25 | dry ice | no |
| polylactide-co-glycolide | 50 | 50 | 0.37 | 35 | no | yes |
| polylactide-co-glycolide | 50 | 50 | 0.37 | 35 | dry ice | no |
| polylactide-co-glycolide | 75 | 25 | 0.20 | 17.5 | no | yes |
| polylactide-co-glycolide | 75 | 25 | 0.20 | 17.5 | dry ice | no |
| polylactide-co-glycolide | 75 | 25 | 0.20 | 25 | no | yes |
| polylactide-co-glycolide | 75 | 25 | 0.20 | 25 | dry ice | no |
| polylactide-co-glycolide | 75 | 25 | 0.20 | 35 | no | yes |
| polylactide-co-glycolide | 75 | 25 | 0.20 | 35 | yes | no |

Accordingly, the carrier provides an environment that provides the advantage of having a sterile polymer with minimal changes in the physical characteristics. This may allow the incorporation of sterile excipient(s) into an aseptic process without the need of additional processing such as grinding or milling the product.

What is claimed is:

1. A package for orienting and cooling a polyester during a polyester sterilization process, the package comprising:
   a plurality of packets each containing polyester granules; and
   a housing defining a receptacle for receiving the plurality of packets and further defining a top region disposed above the receptacle, a bottom region disposed below the receptacle generally opposite the top region, and a plurality of sides disposed around the receptacle between the top region and the bottom region, the housing including
   at least one divider disposed between adjacent packets for separating the packets, and
   a compartment disposed in at least one of the plurality of sides, the compartment receiving a coolant, wherein the coolant is not disposed directly above the receptacle and is not disposed directly below the receptacle such that the receptacle can be irradiated from top to bottom or bottom to top without radiation passing through the coolant.

2. The package of claim 1, wherein the housing further includes a plurality of vents in fluid communication with the compartment for venting the coolant.

3. The package of claim 1, wherein the packets are substantially free of oxygen.

4. The package of claim 1, wherein the at least one divider includes a plurality of generally planar dividers arranged in parallel, one packet being disposed between adjacent dividers.

5. The package of claim 4, wherein the dividers and the packets are arranged face-to-face in a row extending in a direction from one of the plurality of sides to another of the plurality of sides.

* * * * *